United States Patent
Tang

(10) Patent No.: US 9,554,974 B2
(45) Date of Patent: Jan. 31, 2017

(54) ORAL DENTRIFICE POWER AND METHOD

(71) Applicant: Tieh-Chun Tang, Rowland Heights, CA (US)

(72) Inventor: Tieh-Chun Tang, Rowland Heights, CA (US)

( * ) Notice: Subject to any disclaimer, the term of this patent is extended or adjusted under 35 U.S.C. 154(b) by 0 days.

(21) Appl. No.: 14/545,248

(22) Filed: Apr. 13, 2015

(65) Prior Publication Data

US 2016/0220456 A1    Aug. 4, 2016

(51) Int. Cl.
*A61K 8/19* (2006.01)
*A61Q 11/00* (2006.01)
*A61K 8/97* (2006.01)
*A61K 8/368* (2006.01)
*A61K 8/25* (2006.01)
*A61K 8/98* (2006.01)
*A61K 8/24* (2006.01)
*A61K 8/02* (2006.01)
*A61K 8/92* (2006.01)

(52) U.S. Cl.
CPC .......... *A61K 8/19* (2013.01); *A61K 8/022* (2013.01); *A61K 8/24* (2013.01); *A61K 8/25* (2013.01); *A61K 8/368* (2013.01); *A61K 8/922* (2013.01); *A61K 8/97* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 4,547,362 A * | 10/1985 | Winston | A61K 8/19 424/49 |
| 7,083,411 B2 * | 8/2006 | Flemmig | A61K 8/02 424/49 |
| 2010/0143271 A1 * | 6/2010 | Yang | A61K 8/24 424/52 |

OTHER PUBLICATIONS

Yang JianDong, Nanometer lapping technology at high speed, Sci China Ser E-Tech, 2007, 50 (1), 27-38.*
Examiner.com; Pearl powder, eat it, wear it, brush your teeth with it; http://www.examiner.com/article/pearl-powder-eat-it-wear-it-brush-your-teeth-with-it, Mar. 10, 2011.*

* cited by examiner

*Primary Examiner* — Brian Gulledge
*Assistant Examiner* — Celeste A Roney
(74) *Attorney, Agent, or Firm* — Gary C Honeycutt

(57) ABSTRACT

The invention relates to daily necessities of life; and more particularly to a dentifrice powder that promotes oral health, and cleaning for the teeth and gums. One example includes the following ingredients:

| | |
|---|---|
| calcium carbonate | 26-36 parts |
| mineral powder | 6-12 parts |
| foaming agent | 3-7 parts |
| sodium benzoate | 3-7 parts |
| Chinese gall | 1-3 parts |
| hydrated amorphous silica | 2-6 parts |
| aromatic agent | 1.5-2.5 parts |
| wintergreen oil | 1.5 to 2.4 parts |
| sodium monofluorophosphate | 17-22 parts |
| calcium supplements | 17-24 parts |

This dental powder provides the absorption of calcium and trace minerals by the teeth and gums, to promote microcirculation, reduce or eliminate periodontal sores, receding gums, loose teeth, gum bleeding, sensitivity to heat and cold, tooth decay, dental disease the breeding of bacteria, and oral inflammation; and to remove stains from the teeth, including cigarette smoke stain, coffee and tea stains, and black and yellow dye stains.

2 Claims, No Drawings

ORAL DENTRIFICE POWER AND METHOD

TECHNICAL FIELD

The invention relates to oral hygiene, including cleaning of the teeth and gums, and supplemental addition of trace elements and calcium to the teeth and gums.

BACKGROUND

Tooth powder as used in daily life, has a long history. With the continuous development of science and technology, continuous improvement of process equipment and tooth powder developed into various types of toothpaste, and thereafter, increasing the quality and grade of the product, now clean by a single type of toothpaste variety, become the variety is complete, functional diversity, hundreds more functional toothpaste brand, satisfied the needs of different levels of consumption.

Toothpaste roughly divided into: the kinds of antibacterial counter, allergy, detergent whitening, deodorant, methods desensitization toothpaste, etc., the existing dentifrice or toothpaste, its function is single, mostly on a tooth or gum problems has protective effect, and inhibit bacteria, disinfection, deodorization, uses mostly white or add fragrance, etc., using this kind of dentifrice or toothpaste can't guarantee the effect of oral healthcare, if the long-term use of existing a dentifrice or toothpaste, can lead to other breed bacteria, viruses, lead to dental problems. In addition, so existing dentifrice or toothpaste, just go to sterilization, deodorization and whitening, etc., without considering the teeth, gums, and the problem of oral nutrition that is not a fundamental up and strengthened in its teeth, gums, and mouth.

SUMMARY OF THE INVENTION

In order to overcome the shortcomings and the inefficiency of existing technology, the aim of the present invention is to provide a supplementary addition of calcium and trace minerals to the teeth and gums, in order to moisten the gums, increase gum microcirculation, alleviate or eliminate swelling, receding gums, loose teeth, periodontal bleeding gums, hot and cold sensitivity, tooth decay, dental disease, inhibit the breeding of bacteria in the mouth, mouth inflammation, eliminate bad breath, remove the cigarette smoke stain and coffee, tea stain on teeth, eliminate the black and yellow dye stain teeth.

Through the following experiments, dental cleaning and the addition of trace minerals and calcium was achieved by the dentrifice of the invention;

The materials used were:

| | |
|---|---|
| calcium carbonate | 26-36 parts |
| mineral powder | 6-12 parts |
| foaming agent | 3-7 parts |
| sodium benzoate | 3-7 parts |
| Chinese gall | 1-3 parts |
| hydrated amorphous silica | 2-6 parts |
| balmy agent | 1.5-2.5 parts |
| wintergreen oil, | 1.5-2.4 parts |
| sodium monofluorophosphate | 17-22 parts |
| calcium supplements | 17-24 parts |

For better quality tooth powder, include by weight the following materials:

| | |
|---|---|
| calcium carbonate | 28-34 parts |
| mineral powder | 8-10 parts |
| foaming agent | 4-6 parts |
| sodium benzoate | 4-6 parts |
| Chinese gall, | 1.6-2.3 parts |
| hydrated amorphous silica | 4-5 parts |
| balmy agent | 1.8-2.1 parts |
| wintergreen oil, | 1.8-2.2 parts |
| sodium monofluorophosphate | 19-21 parts |
| calcium supplements | 19-21 parts |

For the best quality tooth powder, include the weight ratios of the raw material:

| | |
|---|---|
| calcium carbonate | 32 parts |
| mineral powder | 9 parts |
| foaming agent | 5 parts |
| sodium benzoate | 5 parts |
| Chinese gall | 2 parts |
| hydrated amorphous silica | 3 parts |
| balmy agent | 2 parts |
| wintergreen oil | 2 parts |
| sodium monofluorophosphate | 20 parts |
| calcium supplements | 20 parts |

Mineral powder includes one or more elements selected from potassium, magnesium, sodium, calcium, selenium and iron. The foaming agent includes a refined detergent base.

Among them, the balmy agent described are as mint flavor spices, green tea, citrus flavors or spearmint.

Among them, the calcium supplements including weight of the materials as follows:

| | |
|---|---|
| Pearl | 3 to 7 parts |
| mother of pearl | 8-12 parts |
| red coral | 2-3 parts |
| oyster shell | 20-30 parts |
| shell | 35-55 parts |
| giant clam shell | 5-10 parts |

For the better quality tooth powder, calcium supplements including weight of the raw materials as follows

| | |
|---|---|
| pearl | 4-6 parts |
| mother of pearl | 9-11 parts |
| red coral | 2.2-2.8 parts |
| oyster shell | 22-28 parts |
| clam shell | 40-50 parts |
| giant clam shell | 6-9 parts |

For the best quality tooth powder, calcium supplements including weight of the raw materials as follows:

| | |
|---|---|
| pearl | 5 parts |
| mother of pearl | 10 parts |
| red coral | 2.5 parts |
| oyster shell | 25 parts |
| clam shell | 45 parts |
| giant clam shell | 7.5 parts |

The preparation methods of calcium supplements, includes the following steps.

A, cleaning the selected raw materials, and employ high pressure sand blasting to remove dirt on the surface of the raw material;

B, Grinding each of the raw materials into 200-400 micron particles;

C, Heating in an inert gas to decomposition after primary grinding;

D, Grinding after heat decomposition of the particles into 30-50 micron particles;

E, Nanometer lapping into 0.1-1 nm nano particles

F, Mixing the nanometer material particles according to desired weight ratios to produce calcium supplements.

When processing pearl as described in step C, first heat up to 400-600 degrees C. use heat decomposition for 1.5 to 2.5 h, then heat up to 800-1000 degrees C. for 0.5-1.5 h;

When processing raw mother of pearl, first heat up to 800-1000 degrees C. for 4.5 to 5.5 h, then heat up to 1700-1900 degrees C. for 4-5 h.

When processing red coral, first heat up to 1000-1200 degrees C. for 6.5 to 7.5 h, then heat to 1600-1800 degrees C. for 4.5-5.5 h.

When processing oyster shell for raw material, first heat up to 700-900 degrees C. for 2 to 3 h, then heat up to 1600-1800 degrees C. for 1-2 h.

When processing raw clam shells, first heat up to 500-700 for 2.5 to 3.5 h, then heat up to 1700-1900 degees C. for 1.5-2.5 h.

When processing raw giant clam shell, first heat up to 600-800 degrees C. 3-4 h, then heat up to 1800-2000 degrees C. for 0.8-1.2 h.

The beneficial method of the present invention is:

In practical use, wet toothbrush and then remove excess water, then dip in certain amount of dentifrice, and brush gently on the surface of the teeth and gums for 3 to 5 minutes for the best, and then rinse or gargle with water. The invention a dental cleaning and adding trace elements and calcium dentifrice, is through oral absorption and surface permeability, teeth and gums to supplementary teeth and the body of calcium and trace minerals, dental health, improve the resistance ability of all mouth parts, and the overall function.

The present invention provides a dental cleaning and adding trace elements and calcium dentifrice, it can nourish the gums, gum microcirculation, alleviate or eliminate inflammation, receding gums, loose teeth, periodontal bleeding gums, hot and cold allergy and tooth decay, dental, ensure healthy gums.

The present invention can prevent breeding of bacteria in the mouth, prevent oral cavity inflammation, keep the mouth clean, and ensure oral health.

The invention provides a dental cleaning and adding trace elements and calcium dentifrice, it can eliminate bad breath, remove the cigarette smoke stain and coffee, tea stain on teeth, eliminate the black and yellow die stain teeth, etc., to keep teeth healthy, clean and beautiful.

The invention a dental cleaning and adding trace elements and calcium dentifrice, described calcium supplements using pure natural Marine creatures as raw material, after processing into nanoscale small molecules, it has the characteristics of marine life, has the rich nutrition, it can penetrate the oral absorption and surface of the teeth and gums, to complement the teeth and the human body needs calcium The present invention a dental cleaning and adding trace elements and calcium dentifrice, described the preparation of calcium supplements method is simple, convenient operation and control, stable quality, high yield, can be large-scale industrial production.

The following experiment provides further understanding of the invention.

A kind of oral cleaning and adding trace elements and calcium dentifrice, including the weight of the raw materials:

| | |
|---|---|
| calcium carbonate | 26-36 parts |
| mineral powder | 6-12 parts |
| blowing agent | 3-7 parts |
| sodium benzoate | 3-7 parts |
| Chinese gall | 1-3 parts |
| hydrated amorphous silica | 2-6 parts |
| balmy agent | 1.5-2.5 parts |
| wintergreen oil, | 1.5-2.4 parts |
| sodium monofluorophosphate | 17-22 parts |
| calcium supplements | 17-24 parts. |

The invention provides a dental cleaning and adding trace elements calcium dentifrice, among them, the basic components of calcium carbonate as dentifrice stated, as abrasive, etc. The trace elements include iron, copper, zinc, manganese, and iodine, all of which occur naturally in marine life structures.

Described among them, the mineral powder of the invention is necessary to improve the human body and maintain improved physiological function of the gums and teeth.

Absorption through the surfaces of the mouth and teeth adds calcium and trace minerals group elements to the human body.

Sodium benzoate performs the main role as a preservative, to prevent the dentifrice deterioration, guarantee the stability and quality of the powders, and extending shelf life to facilitate storage.

Gallnut, stated in the powder mainly acts as anti-inflammatory, analgesic, ease the hematoma, stop bleeding gums, antibacterial sterilization, etc., can treat various diseases. In addition, Chinese gall after being absorbed by mouth, but also bloody, night sweats, detoxification, embellish lung, gastric and duodenal ulcers, and has the effect of heat-clearing and detoxifying.

The hydrated amorphous silica is effective in the process of making the tooth powder, as an agent for binding ginseng and other components into tiny particles.

Among them, the balmy agent in the dentifrice described, the main function is to add fragrance to the dentifrice, so that it becomes more suitable and desirable.

Among them, wintergreen oil in the dentifrice described mainly causes detumescence, anti-inflammatory and analgesic effects, stimulate the mouth and the gums, and to promote blood circulation.

Mentioned among them, sodium monofluorophosphate prevents tooth decay, and bactericidal effect of *Aspergillus, Staphylococcus aureus, Salmonella, Pseudomonas aeruginosa* and *Catarrh aureus* have obvious inhibitory effect on the growth and reproduction, but also has the effect of cleaning for your teeth.

Among them, the main effect of calcium supplements absorbed by the teeth and gums, is to stop bleeding, and strengthen teeth.

In practical use, the realization of this dentifrice ready, wet toothbrush after get rid of excess water, then dip in take a certain amount of dentifrice, will carry dentifrice toothbrush gently on the surface of the teeth and gums friction 3 to 5 minutes for the best, and then gargle with water or mouthwash.

The invention provides a dental cleaning and adding trace elements and calcium dentifrice, through oral absorption and surface permeability, teeth and gums to supplementary teeth and the body of calcium and trace minerals, dental health, improve the resistance ability of oral cavity and the overall function.

The present invention, in addition to dental cleaning and adding trace elements and calcium dentifrice, it can nourish the gum, gum microcirculation, alleviate or eliminate swelling, receding gums, loose teeth, periodontal bleeding gums, hot and cold sensitivity and tooth decay, dental, ensure healthy gums.

The dentrifice of present invention can effectively inhibit the breeding of bacteria in the mouth, prevent oral cavity inflammation, keep the mouth clean, ensuring oral health.

The invention a dental cleaning and adding trace elements and calcium dentifrice, it can eliminate bad breath, remove the cigarette smoke stain and coffee, tea stain on teeth, eliminate the black and yellow die stain teeth, etc., to keep teeth healthy, clean and beautiful

EXAMPLE 1

A kind of oral cleaning and adding trace elements and calcium dentifrice, including the weight of the raw material as follows:

| | |
|---|---|
| calcium carbonate | 36 parts |
| mineral powder | 6 parts |
| blowing agent | 3 parts |
| sodium benzoate | 3 parts |
| Chinese gall | 1 part |
| hydrated amorphous silica | 2 parts |
| balmy agent | 1.5 parts |
| wintergreen oil | 1.5 parts |
| sodium monofluorophosphate | 17 parts |
| calcium supplements | 24 parts |

Described in this example, mineral powder as potassium, magnesium, sodium, calcium, selenium and iron one or more of the powder. In this example, the foaming agent is a refined detergent base Described the implementation of the case, the balmy agent for mint flavor spices, green tea, citrus flavours or spearmint In this example, calcium supplements including weight of the raw materials as follows:

| | |
|---|---|
| pearl | 3 parts |
| mother of pearl | 8 parts |
| red coral | 2 parts |
| oyster shell | 20 parts |
| clam shell | 55 parts |
| giant clam shell | 5 parts |

Described the implementation of the case, the method of preparation of calcium supplements, includes the following steps:
A, cleaning the selected raw material, and use high pressure sand blasting to remove dirt on the surface of the material
B, grinding materials after cleaning into 200-400 micron particles;
C, heat decomposition: in inert gas particles after the primary grinding heat decomposition,
D, rules grinding: grinding after heat decomposition of the particles into 30-50 microns particles
E, nanometer lapping, after grinding particle grinding into 0.1 1 nm nano particles F, mixing, mixing ratio of each raw material particles according to weight, to produce calcium supplements The implementation of the case, as described in step C, for pearl, first heat up to 400-600 degrees C. heat decomposition of 1.5 to 2.5 h, then heat up to 800-1000 degrees C. for 0.5-1.5 h.

For the mother of pearl, first heat up to 800-1000 degrees C. for 4.5 to 5.5 h, then heat up to 1700-1900 degrees C. for 4-5 h.

For the red coral, first heat up to 1000-1200 degrees C. for 6.5 to 7.5 h, then heat up to 1600-1800 degrees C. for 4.5-5.5 h.

For oyster shell, first heat up to 700-900 degrees C. for 2 to 3 h, then heat up to 1600-1800 degrees C. for 1-2 h.

For clam shells, first heat up to 500-700 degrees C. for 2.5 to 3.5 h, then heat up to 1700-1900 degrees C. for 1.5-2.5 h.

For giant clam shell, first heat up to 600-800 degrees C. for 3-4 h, then heat up to 1800-2000 degrees C. for 0.8 1.2 h.

This example for this oral cavity clean and supplement of trace elements and calcium powder dentifrice better implementation example, the tooth powder through oral absorption and surface permeability, teeth and gums to supplementary teeth and the body of calcium and trace minerals, dental health, improve the resistance ability of oral cavity and the overall function; The tooth powder can nourish your gums, make gum microcirculation, alleviate or eliminate swelling, receding gums, loose teeth, periodontal bleeding gums, hot and cold allergy and tooth decay, dental, ensure healthy gums; The tooth powder can effectively inhibit the breeding of bacteria in the mouth, mouth inflammation to prevent foaming, keep the mouth clean, ensure that oral health; The tooth powder can eliminate bad breath, remove the cigarette smoke stain and coffee, tea stain on teeth, eliminate the black and yellow die stain teeth, etc., to keep teeth healthy, clean and beautiful. Described the implementation of the case, the calcium supplements using pure natural marine creatures as raw material, after processing into nanoscale small molecules, it has the characteristics of Marine organisms, has rich nutrition, it can penetrate the oral surfaces for absorption into surface of the teeth and gums, to provide necessary calcium.

In this example, described the preparation of calcium supplements method is simple, convenient operation and control, stable quality, high yield, can be large-scale industrial production.

EXAMPLE 2

A kind of oral cleaning and adding trace elements and calcium dentifrice, including the weight of the raw material as follows:

| | |
|---|---|
| calcium carbonate | 26 parts |
| mineral powder | 12 parts |
| blowing agent | 7 parts |
| sodium benzoate | 7 parts |
| Chinese gall | 3 parts |
| hydrated amorphous silica | 6 parts |
| balmy agent | 12.5 parts |
| wintergreen oil | 2.4 parts |
| sodium monofluorophosphate | 22 parts |
| calcium supplements | 17 parts |

Described in this example, mineral powder as potassium, magnesium, sodium, calcium, selenium and iron one or more of the powder.

In this example, the foaming agent is refined detergent base.

Described the implementation of the case, the balmy agent for mint flavor spices, green tea, citrus flavours or spearmint In this example, described in the calcium supplements include by weight of the raw material:

| | |
|---|---|
| pearl | 7 parts |
| mother of pearl | 12 parts |
| red coral | 3 parts |
| oyster shell | 30 parts |
| clam shell | 35 parts |
| giant clam shell | 10 parts |

Described the implementation of the case, the method of preparation of calcium supplements, includes the following steps:
A, cleaning the selected raw materials, and adopt the way of high pressure sand blasting to remove dirt from the surfaces of the material
B, the primary grinding: grinding particles into a 200-400 micron size.
C, heat decomposition: in an inert gas to heat decomposition after primary grinding particles.
D, grinding after heat decomposition of the particles into 30-50 micron particles.
E, nanometer lapping: rules after grinding particle grinding into 0.1-1 nm nano particles
F, mixing: mixing ratio of each raw material particles according to the weight, produce calcium supplements The implementation of the case, as described in step C, the raw pearl is first heated up to 400-600 degrees C. for heat decomposition for 1.5 to 2.5 h, then heat up to 800-1000 degrees for 0.5-1.5 h.

Raw materials for the mother of pearl, the first heat up to 800-1000 degrees C. heat decomposition for 4.5 to 5.5 h, then heat up to 1700-1900 degrees C. for 4-5 h;

Raw materials for the red coral, the first heat up to 1000-1200 degrees C. for 6.5 to 7.5 h, then heat up to 1600-1800 degrees C. for 4.5-5.5 h.

Oyster shell for raw material, the first heat up to 700-900 degrees C. for 3 h, then heat up to 1600-1800 degrees C. for 1-2 h;

Raw materials for clam shells, the first heat up to 500-700 degrees C. for 2.5 to 3.5 h, then heat up to 1700-1900 degrees for 1.5-2.5 h.

Raw materials for the Giant clam shells, first heat up to 600-800 degrees for 3-4 h, then heat up to 1800-2000 degrees C. for 0.8-1.2 h.

This example for this oral cavity clean and supplement of trace elements and calcium powder dentifrice better implementation example, the tooth powder through oral absorption and surface permeability, teeth and gums to supplementary teeth and the body of calcium and trace minerals, dental health, improve the resistance ability of oral cavity and the overall function; The tooth powder can nourish your gums, make gum microcirculation, alleviate or eliminate swelling, receding gums, loose teeth, periodontal bleeding gums, hot and cold allergy and tooth decay, dental, ensure healthy gums; The tooth powder can effectively inhibit the breeding of bacteria in the mouth, mouth inflammation to prevent foaming, keep the mouth clean, ensure that oral health; The tooth powder can eliminate bad breath, remove the cigarette smoke stain and coffee, tea stain on teeth, eliminate the black and yellow die stain teeth, to keep teeth healthy, clean and beautiful. The implementation of the calcium supplements using pure natural marine creatures as raw material, after processing into nanoscale small particles, it has the characteristics of marine organisms, has rich nutrition, it can penetrate into the surface of the teeth and gums, to complement the teeth and the human body with necessary calcium.

This example of the preparation of calcium supplements method is simple, convenient operation and control, stable quality, high yield, can be large-scale industrial production.

EXAMPLE 3

A kind of oral cleaning and adding trace elements and calcium dentifrice, including by weight of the raw material:

| | |
|---|---|
| calcium carbonate | 34 parts |
| mineral powder | 8 parts |
| foaming agent | 4 parts |
| sodium benzoate | 4 parts |
| Chinese gall | 1.6 parts |
| hydrated amorphous silica | 4 parts |
| balmy agent | 1.8 parts |
| wintergreen oil | 1.8 parts |
| sodium monofluorophosphate | 19 parts |
| calcium supplements | 21 parts |

As described in this example, mineral powder is potassium, magnesium, sodium, calcium, selenium and iron one or more of the powder.

Described the implementation of the case, the balmy agent for mint flavor spices, green tea, citrus flavors or spearmint In this example, the calcium supplements include by weight:

| | |
|---|---|
| pearl | 4 parts |
| mother of pearl | 9 parts |
| red coral | 2.2 parts |
| oyster shell | 22 parts |
| clam shell | 50 parts |
| giant clam shell | 6 parts |

In this example, the method of preparation of calcium supplements, includes the following steps:
A, cleaning of the selected raw materials, use high pressure sand blasting to remove dirt on the surface of the material;
B, primary grinding, after cleaning the raw material, grinding particles into a 200-400 micron size;
C, heat decomposition in an inert gas, after primary grinding particles
D, then grinding after heat decomposition of the particles into 30-50 micron particles
E, nanometer lapping after grinding particle, further grinding into 0.1-1 nm nano particles;
F, then mixing the nanometer raw material particles according to the desired weight ratios, to produce the calcium supplements.

As described in step C, when the raw material is pearl, first heat up to 400-600 degrees C. for 1.5 to 2.5 h, then heat up to 800-1000 degrees C. for 0.5-1.5 h.

When mother of pearl is selected, first heat at 800-1000 degrees C. for 4.5 to 5.5 h, then heat at 1700-1900 degrees C. for 4 to 5 h.

For red coral, first heat at 1000-1200 degrees C. for 6.5 to 7.5 h, then heat at 1600-1800 degrees for 4.5-5.5 h;

For oyster shell as raw material, first heat at 700-900 degrees C. for 2 to 3 h, then heat at 1600-1800 degrees C. for 1-2 h;

For clam shells, first heat at 500-700 degrees C. for 2.5 to 3.5 h, then heat up to 1700-1900 degrees C. for 1.5-2.5 h For giant clam shells, first heat at 600-800 degrees C. for 3-4 h, then heat at 1800-2000 degrees C. for 0.8 1.2 h.

This example for this oral cavity clean and supplement of trace elements and calcium powder dentifrice better implementation example, the tooth powder through oral absorption and surface permeability, teeth and gums to supplementary teeth and the body of calcium and trace minerals, dental health, improve the resistance ability of oral cavity and the overall function; The tooth powder can nourish your gums, make gum microcirculation, alleviate or eliminate swelling, receding gums, loose teeth, periodontal bleeding gums, hot and cold allergy and tooth decay, dental, and ensure healthy gums. The tooth powder can effectively inhibit the breeding of bacteria in the mouth, mouth inflammation, keep the mouth clean, and ensure oral health. The tooth powder can eliminate bad breath, remove the cigarette smoke stain and coffee, tea stain on teeth, eliminate the black and yellow die stain teeth, etc., to keep teeth healthy, clean and beautiful The calcium supplements using pure natural marine creatures as raw material, after processing into nanoscale particles, it has the characteristics of marine organisms, has rich nutrition, it can penetrate the oral and mouth surfaces of the teeth and gums, to complement the teeth and provide more calcium to the human body.

In this example, described the preparation of calcium supplements method is simple, convenient operation and control, stable quality, high yield, can be large-scale industrial production.

EXAMPLE 4

A kind of oral cleaning and adding trace elements and calcium dentifrice, including by weight as follows:

| | |
|---|---|
| calcium carbonate | 34 parts |
| mineral powder | 10 parts |
| frother | 6 parts |
| sodium benzoate | 6 parts |
| Chinese gall | 2.3 parts |
| hydrated amorphous silica | 5 parts |
| balmy agent | 2.1 parts |
| wintergreen oil | 2.2 parts |
| sodium monofluorophosphate | 21 parts |
| calcium supplements | 19 parts |

In this example, mineral powder includes potassium, magnesium, sodium, calcium, selenium and iron one or more of the powder.

In this example, the foaming agent is refined detergent base.

Described the implementation of the case, the balmy agent for mint flavor spices, green tea, citrus flavors or spearmint.

In this example, calcium supplements including by weight as follows:

| | |
|---|---|
| pearl | 6 parts |
| mother of pearl | 11 parts |
| red coral | 2.8 parts |
| oyster shell | 28 parts |
| clam shell | 40 parts |
| giant clam shell | 9 parts |

The method of preparation of calcium supplements includes the following steps:

A, cleaning the selected raw materials, and use high pressure sand blasting to remove dirt from the surface of the material;

B, the primary grinding, after cleaning the raw material, grinding particles to a 200-400 micron size;

C, heat decomposition in an inert gas to heat decomposition after primary grinding particles;

D, after heat decomposition grinding the particles to 30-50 micron size particles;

E, nanometer lapping: grinding particles to 0.1-1 nm nano particles;

F, mixing the nanometer particles according to the desired weight ratios to produce calcium supplements.

The implementation of the case, as described in step C, when processing pearl, first heat at 400-600 degrees C. for 1.5 to 2.5 h, then heat at 800-1000 degrees C. for 0.5-1.5 h.

When processing mother of pearl, first heat up to 800-1000 degrees C. for 4.5 to 5.5 h, then heat at 1700-1900 degrees C. for 4 to 5 h.

For red coral, first heat at 1000-1200 degrees C. for 6.5 to 7.5 h, then heat at 1600-1800 degrees C. for 4.5-5.5 h.

For oyster shell, first heat at 700-900 degrees C. for 2 to 3 h, then heat at 1600-1800 degrees C. for 1-2 h.

For clam shells, first heat at 500-700 degrees C. for 2.5 to 3.5 h, then heat at 1700-1900 degrees C. for 1.5 2.5 h.

For giant clam shells, first heat at 600-800 degrees C. for 3-4 h, then heat at 1800-2000 degrees C. for 0.8 1.2 h.

This example for this oral cavity clean and supplement of trace elements and calcium powder dentifrice better implementation example, the tooth powder through oral absorption and surface permeability, teeth and gums to supplementary teeth and the body of calcium and trace minerals, dental health, improve the resistance ability of oral cavity and the overall function. The tooth powder can nourish your gums, make gum microcirculation, alleviate or eliminate swelling, receding gums, loose teeth, periodontal bleeding gums, hot and cold allergy and tooth decay, dental, ensure healthy gums. The tooth powder can effectively inhibit the breeding of bacteria in the mouth, mouth inflammation to prevent foaming, keep the mouth clean, ensure that oral health; The tooth powder can eliminate bad breath, remove the cigarette smoke stain and coffee, tea stain on teeth, eliminate the black and yellow die stain teeth, etc., to keep teeth healthy, clean and beautiful. The calcium supplements using pure natural marine creatures as raw material, after processing into nanoscale small molecules, it has the characteristics of marine organisms, has rich nutrition, it can penetrate the oral absorption and surface of the teeth and gums, to complement the teeth and provide necessary calcium for the human body.

In this example, described the preparation of calcium supplements method is simple, convenient operation and control, stable quality, high yield, can be large-scale industrial production.

EXAMPLE 5

A kind of oral cleaning dentifrice for adding trace elements and calcium, including by weight:

| | |
|---|---|
| calcium carbonate | 32 parts |
| mineral powder | 9 parts |
| blowing agent | 5 parts |
| sodium benzoate | 5 parts |
| Chinese gall | 2 parts |
| hydrated amorphous silica | 3 parts |
| balmy agent | 2 parts |
| wintergreen oil | 2 parts |
| sodium monofluorophosphate | 20 parts |
| calcium supplements | 20 parts |

In this example, the mineral powder includes one or more of potassium, magnesium, sodium, calcium, selenium and iron. The foaming agent includes a refined detergent base.

The balmy agent includes mint flavor spices, green tea, citrus flavours or spearmint.

This example, includes by weight:

| | |
|---|---|
| pearl | 5 parts |
| mother of pearl | 10 parts |
| red coral | 2.5 parts |
| oyster shell | 25 parts |
| clam shell | 45 parts |
| giant clam shell | 7.5 parts |

The method of preparation of calcium supplements, includes the following steps:

A, cleaning the selected raw materials with high pressure sand blasting to remove dirt from the surfaces of the material;
B, primary grinding to a particle size of 200-400 microns;
C, heat decomposition in an inert gas, after primary grinding particles;
D, grinding after heat decomposition to a particle size of 30-50 microns;
E, nanometer lapping to grind particles into 0.1-1 nm nano particles;
F, mixing the nanometer particles by weight, to produce calcium supplements.

For processing raw pearl, first heat at 400-600 degrees C. for 1.5 to 2.5 h, then heat at 800-1000 degrees C. for 0.5-1.5 h.

For mother of pearl, first heat at 800-1000 degrees C. for 4.5 to 5.5 h, then heat at 1700-1900 degrees C. for 4-5 h;

For red coral, first heat at 1000-1200 degrees C. for 6.5 to 7.5 h, then heat at 1600-1800 degrees C. for 4.5-5.5 h.

For oyster shell, first heat at 700-900 degrees C. for 2 to 3 h, then heat at 1600-1800 degrees C. for 1-2 h.

For clam shells, first heat at 500-700 degrees C. for 2.5 to 3.5 h, then heat at 1700-1900 degrees C. for 1.5-2.5 h.

For giant clam shells, first heat at 600-800 degrees C. for 3-4 h, then heat at 1800-2000 degrees C. for 0.8-1.2 h.

This example for this oral cavity clean and supplement of trace elements and calcium powder dentifrice better implementation example, the tooth powder through oral absorption and surface permeability, teeth and gums to supplementary teeth and the body of calcium and trace minerals, dental health, improve the resistance ability of oral cavity and the overall function; The tooth powder can nourish your gums, make gum microcirculation, alleviate or eliminate swelling, receding gums, loose teeth, periodontal bleeding gums, hot and cold allergy and tooth decay, dental, ensure healthy gums; The tooth powder can effectively inhibit the breeding of bacteria in the mouth, mouth inflammation, keep the mouth clean, and ensure oral health. The tooth powder can eliminate bad breath, remove the cigarette smoke stain and coffee, tea stain on teeth, eliminate the black and yellow die stain teeth, etc., to keep teeth healthy, clean and beautiful.

Described the implementation of the case, the calcium supplements using pure natural marine creatures as raw material, after processing into nanoscale particles it has the characteristics of marine organisms, has rich nutrition, it can penetrate the oral surfaces of the teeth and gums, to complement the teeth and provide the body with necessary calcium.

In this example, the preparation of calcium supplements method is simple, convenient operation and control, stable quality, high yield, can be large-scale industrial production.

In the above example of the invention better implementation scheme, in addition to this, the present invention can also be the other way, on the premise of not out of the present invention idea any obvious replacement within the scope of protection of the present invention.

The invention claimed is:

1. A method for the large scale industrial production of a dentifrice powder containing pure nano calcium supplements obtained from raw materials including 4-6 parts pearl, 9-11 parts mother of pearl, 2.2-2.8 parts red coral, 22-28 parts oyster shells, 40-50 parts clam shells, and 6-9 parts giant clam shells, comprising the following steps, applied separately to each of said raw materials:
   A. sand blasting each raw material to remove surface contaminants,
   B. grinding each raw material into 200-400 micron particles,
   C. heating said particles in inert gas to a decomposition temperature,
   D. grinding again after decomposition, until 30-50 micron particles are obtained,
   E. nanometer lapping until one nanometer calcium supplements are obtained,
   F. mixing the supplements obtained from step E for each raw material, and then
   G. formulating a dentifrice powder containing said mixed supplements.

2. A method as in claim 1 wherein step C for pearl includes first heating to 400-600 degrees C. for 1.5-2.5 hours, then heating to 800-1000 degrees C. for 0.5 to 1.5 hour; step C for mother of pearl includes first heating to 800-1000 degrees C. for 4.5-5.5 hours, then heating to 1700-1900 degrees C. for for 4 to 5 hours; step C for red coral includes first heating to 1000-1200 degrees C. for 6.5-7.5 hours, then heating to 1600-1800 degrees C. for 4.5-5.5 hours; step C for oyster shells includes first heating to 700-900 degrees C. for 2 to 3 hours, then heating to 1600-1800 degrees C. for 1 to 2 hours; step C for clam shells includes first heating to 500-700 degrees C. for 2.5-3.5 hours, then heating to 1700-1900 degrees C. for 1.5-2.5 hours; step C for giant clam shells includes first heating to 600-800 degrees C. for 3 to 4 hours, then heating to 1800-2000 degrees C. for 0.8 to 1.2 hours.

* * * * *